United States Patent [19]

Huefner et al.

[11] Patent Number: 5,163,917
[45] Date of Patent: Nov. 17, 1992

[54] BARREL MOUNTED NEEDLE GUARD FOR HYPODERMIC SYRINGES

[76] Inventors: Norman Huefner, 11 Lindall, Laguna Niguel, Calif. 92677; Frank J. Burrell, Jr., 22504 Warmside Ave., Torrance, Calif. 90505

[21] Appl. No.: 765,873

[22] Filed: Sep. 26, 1991

[51] Int. Cl.⁵ ............................................. A61M 5/00
[52] U.S. Cl. ...................................... 604/198; 604/263
[58] Field of Search ............... 604/195, 198, 110, 263, 604/187, 232

[56] References Cited

U.S. PATENT DOCUMENTS

| | | | |
|---|---|---|---|
| 4,122,836 | 10/1978 | Burnett | 604/187 X |
| 4,743,233 | 5/1988 | Schneider | 604/198 |
| 4,915,701 | 4/1990 | Halkyard | 604/232 X |
| 5,066,277 | 11/1991 | Carrell et al. | 604/195 |

Primary Examiner—John D. Yasko
Attorney, Agent, or Firm—Gilbert Kivenson

[57] ABSTRACT

A tubular guard for syringes which can be slid up or down along the barrel and has provision for locking in either a "needle safe" or "needle exposed" position. The guard can also be arranged to allow for automatic withdrawal as part of the injecting process.

1 Claim, 2 Drawing Sheets

BARREL MOUNTED NEEDLE GUARD FOR HYPODERMIC SYRINGES

BACKGROUND OF THE INVENTION

It is estimated that some 800,000 health care workers accidentally receive stab wounds each year from hypodermic syringe needles used in their work. This has been of increasing concern because of the spread of deadly infections which is traceable in part to these accidents.

Prior art has employed various types of needle shields but problems have arisen when the shield is to be replaced after partial or full injection of a syringe's contents. The return of the needle to the sheath requires good depth perception because of the relatively small angle of acceptance of the sheath. If an error is made, there is a danger that the technician can thrust the needle into the hand holding the sheath. The prior art of Heydrich (U.S. Pat. No. 2,854,976) and Smith (U.S. Pat. No. 4,643,722) treats this problem by sheath constructions which fit over a needle through a side opening. The sheathing motion is thus perpendicular to the penetrating motion; the likelihood of accidental puncture is thus reduced. In some cases, such as the injection of anesthetics in dentistry, however, the syringe is applied at a number of points. The inconvenience of finding and applying the sheath after each injection discourages its use.

Other problems with prior needle protection devices are with their sterilizability. Close fitting sheaths tend to seal off the needle from the entrance of liquids and gases. The original cleanliness of the needle is thus guarded but a problem develops if the technician attempts to resterilize the sheath.

OBJECTIVES AND SUMMARY OF THE INVENTION

It is one objective of the present invention to provide a barrel-mounted, slidable needle shield which can be readily moved to expose the needle and just as readily repositioned to prevent accidents.

It is a second objective of the present invention to provide a low cost, easily mounted and demounted shield which can be replaced after each series of injections. The barrel-mounted guard is slid forward to shield the needle and backward to expose it. The guard may be retained in the "needle exposed" or "needle shielded" positions by various mechanisms utilizing threads, flexible projections, a magnet or a spring.

The present invention mounts on the barrel of a conventional hypodermic syringe using a retaining washer which is held in place by the threaded end piece now provided on these syringes.

DETAILED DESCRIPTION OF THE INVENTION

Figure 1:
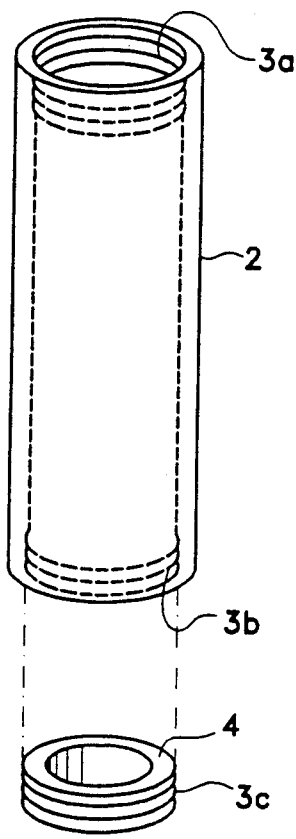
FIG. 1 is a perspective view of a preferred embodiment of the invention showing the cylindrical shield and its retaining washer.

The operation of the invention will now be described with initial reference to FIGS. 1 and 2. A hollow cylinder 2 is utilized to provide shielding for the needle. The cylinder is internally threaded at points 3a and 3b near its top and bottom ends. The inside diameter of the cylinder is such as to loosely slide over barrel 19 of the hypodermic syringe.

A support washer 4 is externally threaded at area 3c so as to engage with the threads 3a and 3b in the cylinder.

Figure 2:
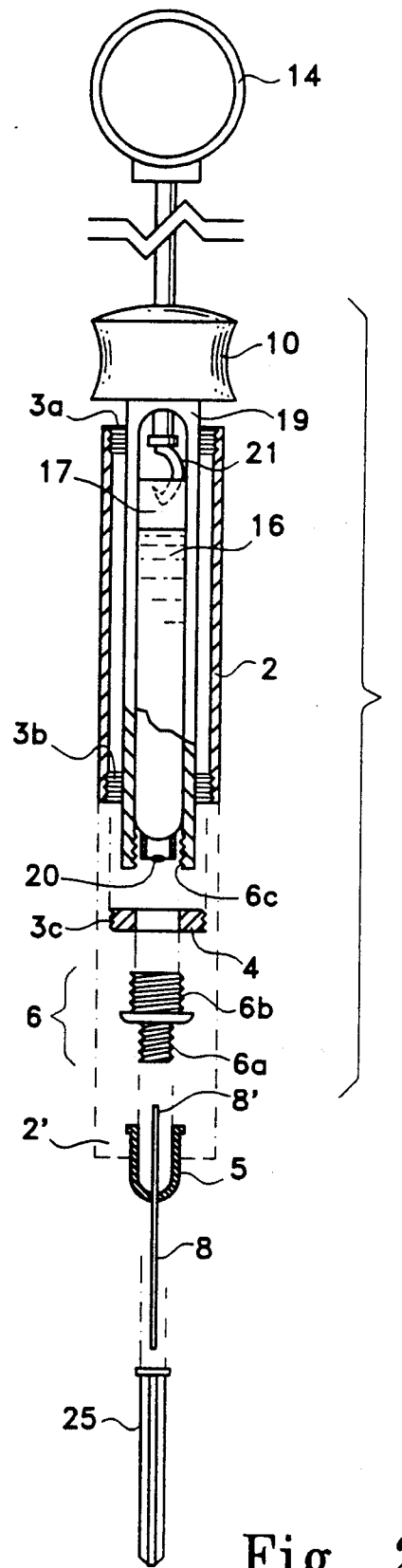
FIG. 2 is a side, expanded view of the invention in place on one type of anesthetic syringe with the shield in the retracted—needle exposed—position.

Syringe 1 in FIG. 2 is of a design often used to inject anesthetics in dentistry. This syringe utilizes a replaceable, cartridge type of ampoule 16 which is provided with a rubber piston 17 at its open end and a rubber gasket seal 20 at the other end.

The procedure for use of this preferred embodiment of the invention would be as follows:

a. the washer 4 is joined to the body 19 of the syringe by means of the end piece 6, the internal thread 6c being engaged by the external thread 6b. This installation would be semi-permanent. The washer 4 remains on the syringe body and can be used with a large number of disposable shield bodies 2. The washer can be serialized along with the syringe body.

b. a disposable needle 8 is then attached to the syringe by means of the threads 6a and the internal threads of the ferrule 5. At this point the needle cover 25 (which is provided with the needle) remains in place for protection against accidental stabs during this assembly sep;

c. the shield of the present invention is then placed over the needle in the "guarding" position, i.e. the threads 3a engage threads 3c;

d. when the type of injection to be given is determined, the thumb ring 14 is pulled out to its extreme open position and am ampoule 16 of the desired material is loaded into the syringe.

e. when it is desired to administer the injection, the thumb ring 14 is pushed in until the harpoon 21 enters the rubber piston 17. This movement also causes the upper extension 8' of the needle to puncture the rubber gasket 20 at the bottom of the ampoule. Shield 2 is next turned counterclockwise until threads 3a disengage from threads 3c which allows shield 2 to be slid up over the barrel 19 and the threads 3c to engage threads 3b thus positioning the shield in its "non-guarding" mode. The needle cover 25 is next removed and discarded.

f. after the injection is given, shield 2 is turned clockwise until threads 3b disengage threads 3c. The shield may now be slid down to its guarding position. Further clockwise turning again fixes the shield in the down position by means of threads 3a and 3c. At this point the chance of accidental contact of needle 8 with outside surfaces or parts of the body is greatly reduced.

The shield is readily withdrawn and returned in the same manner for multiple injections; ampoules may be added or the syringe temporarily placed on a working surface with minimum danger of accidental stabbing. When the injecting of a particular patient is finished, the needle, ampoule and shield can be discarded.

The shield is preferably made of clear plastic so that the position of piston 17 and the amount of liquid remaining can continue to be observed as the syringe is being used.

The threaded washer can be fabricated as part of the syringe barrel.

Figure 3:
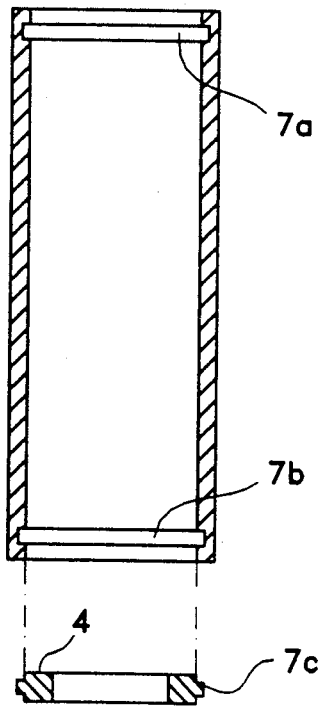
FIG. 3 is a cross section of the invention using a second embodiment of a means for retention of the shield.

The application of a second embodiment of the shield retaining means is shown in FIG. 3. In this modification the threads 3a and 3b have been replaced by the grooves 7a and 7b. The washer 4 has the protrusion 7c along tis circumference which can enter the grooves. The usher can be constructed of a resilient material such as nylon or teflon. Retention of the shield in the guarding or non-guarding position is obtained by axial pressure which forces protrusion 7c into groove 7a or 7b.

Figure 4:
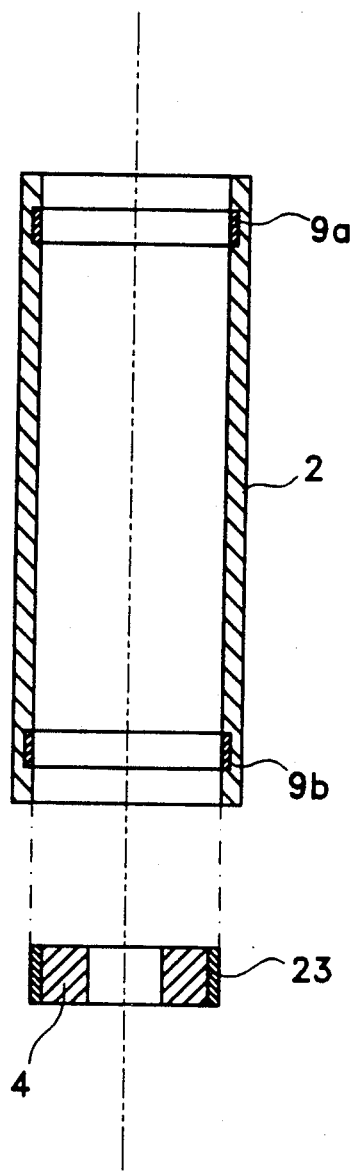
FIG. 4 is a cross section of the invention using a third embodiment of a means for retention of the shield.

A third embodiment of the retaining means, shown in FIG. 4, utilizes two steel rings 9a and 9b which are imbedded in shield 2 and a ring magnet 23 fixed in the rim of washer 4. The shield is held in place in the guarded and unguarded positions by the attraction between magnet 23 and the steel rings.

The invention has been described with reference to a particular type of hypodermic syringes. It may also be adapted to other types of syringes used in dentistry and medicine.

Figure 5:
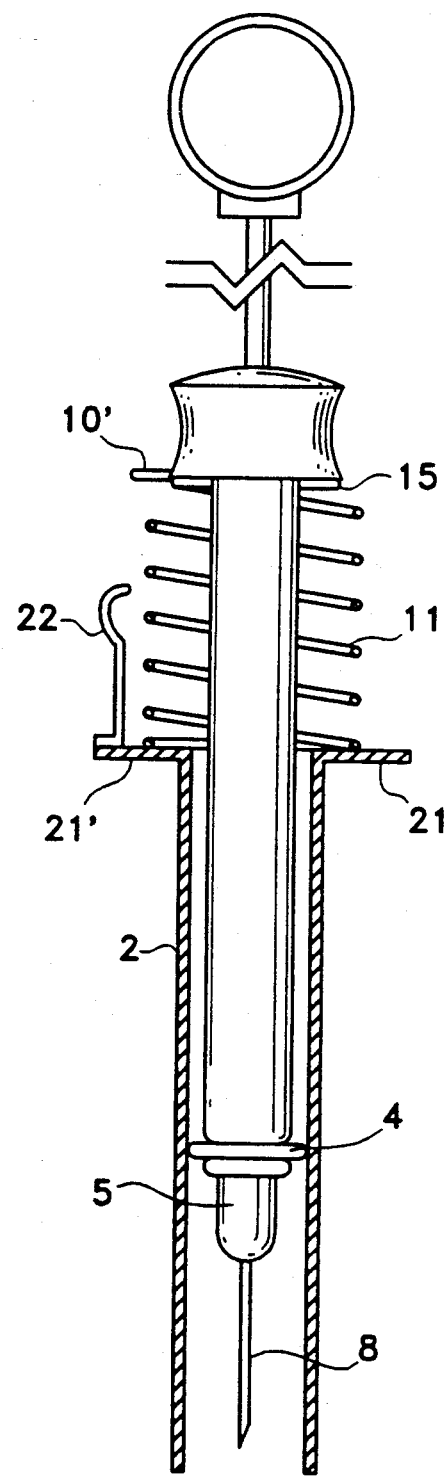
FIG. 5 is a side cross sectional view of the invention using a fourth embodiment of a means for retention of the shield.

A fourth embodiment of the shield retaining means is illustrated in FIG. 5. The shield is provided in this cases with lugs 21 and 21' to accommodate the first and second flanges and hold one end of a compression spring 11. The other end of the spring is provided with a layer of contact adhesive 15 to hold it against the end piece 10 of the syringe. The resilient force of spring 11 is chosen so that the pressure exerted between the thumb ring 14 and the finger lugs 21 and 22 moves the shield and exposes the needle before liquid is expelled. If pressure is let up, the shield returns automatically to the protective position. An optional latching hook 22, attached to lug 21', will encounter endpiece 10' at the end of the compression of spring 11, temporarily locking the shield in the open position for use with those injection techniques which require reversal of the syringe plunger, e.g. aspirating procedures.

We claim:

1. A retractable needle shield for use with a hypodermic syringe having a plunger and a barrel comprising:
   a. a hollow cylinder which slidably encloses the barrel of said syringe and contains one part of a restraining means on its inner surface at both ends;
   b. a washer held in place near the bottom of the barrel which is provided with a second part of the restraining means; whereby the hollow cylinder can be retained by means of the first restraining means to expose the needle of the syringe, the first restraining means then released and the cylinder slid along the barrel to a position where it covers the needle and is held there by the second part of the retraining means which is formed of threads on the inside surface of the cylinder at both ends and on the outside diameter of the washer.

* * * * *